(12) United States Patent
Grandbois et al.

(10) Patent No.: US 9,199,899 B2
(45) Date of Patent: Dec. 1, 2015

(54) PROCESS FOR THE PRODUCTION OF CHLORINATED ALKANES

(71) Applicants: Matthew L. Grandbois, Midland, MI (US); Xiaoyun Chen, Midland, MI (US); William J. Kruper, Jr., Sanford, MI (US)

(72) Inventors: Matthew L. Grandbois, Midland, MI (US); Xiaoyun Chen, Midland, MI (US); William J. Kruper, Jr., Sanford, MI (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

(21) Appl. No.: 14/362,249

(22) PCT Filed: Nov. 30, 2012

(86) PCT No.: PCT/US2012/067261
§ 371 (c)(1),
(2) Date: Jun. 2, 2014

(87) PCT Pub. No.: WO2013/082404
PCT Pub. Date: Jun. 6, 2013

(65) Prior Publication Data
US 2014/0323775 A1    Oct. 30, 2014

Related U.S. Application Data

(60) Provisional application No. 61/566,202, filed on Dec. 2, 2011.

(51) Int. Cl.
*C07C 17/013* (2006.01)
*C07C 17/10* (2006.01)

(52) U.S. Cl.
CPC ............. *C07C 17/013* (2013.01); *C07C 17/10* (2013.01)

(58) Field of Classification Search
CPC ........ C07C 17/013; C07C 17/06; C07C 17/10
USPC ........................................................ 570/261
See application file for complete search history.

(56) References Cited

U.S. PATENT DOCUMENTS

| | | |
|---|---|---|
| 2,119,484 A | 5/1938 | Levine |
| 2,179,378 A | 11/1939 | Metzger |
| 2,207,193 A | 7/1940 | Groll |
| 2,299,441 A | 10/1942 | Vaughn |
| 2,302,228 A | 11/1942 | Kharasch |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Elton |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Weirsum |
| 3,954,410 A | 5/1976 | Pohl et al. |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |

(Continued)

FOREIGN PATENT DOCUMENTS

| | | |
|---|---|---|
| CH | 609022 | 6/1974 |
| CN | 101215220 | 7/2008 |

(Continued)

OTHER PUBLICATIONS

Ochi, et al., "Preparation of Chloropropenes by Photochemical Dehydrochlorination of 1,2-Dichloropropane", Chemical Abstracts, Jul. 17, 1989, p. 574, 111(3).

(Continued)

*Primary Examiner* — Shailendra Kumar

(57) ABSTRACT

Processes for the production of chlorinated alkanes are provided. The present processes comprise catalyzing the addition of at least two chlorine atoms to an alkane and/or alkene with a catalyst system comprising one or more nonmetallic iodides and/or lower than conventional levels of elemental iodine and at least one Lewis acid. The present processes make use of sulfuryl chloride, or chlorine gas, as a chlorinating agent.

14 Claims, No Drawings

(56) References Cited

U.S. PATENT DOCUMENTS

| | | |
|---|---|---|
| 4,661,648 A | 4/1987 | Frankllin |
| 4,702,809 A | 10/1987 | Mueller |
| 4,714,792 A | 12/1987 | Mueller |
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Mueller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo |
| 8,581,012 B2 | 11/2013 | Tirtowidjojo |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi et al. |
| 2002/0110711 A1 | 8/2002 | Boneberg et al. |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0088547 A1 | 4/2009 | Schamshurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose et al. |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |

(56) References Cited

FOREIGN PATENT DOCUMENTS

| | | |
|---|---|---|
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |
| JP | 2001-151708 | 6/2001 |
| JP | 2001-213820 | 8/2001 |
| JP | 2006-272267 | 10/2006 |
| JP | 2007-021396 | 2/2007 |
| JP | 2008-063314 | 3/2008 |
| JP | 2009-000592 | 1/2009 |
| JP | 2009-046653 | 3/2009 |
| JP | 2011-144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Bai et al., "Isomerization of Tetrachloropropene to Promote Utilization Ratio of Triallate Raw Materials" Petrochemical Technology & Application, 2007, 25(1).

Boualy et al., "Kharasch Addition of Tetrachloromethane to Alkenes Catalyzed by Metal Acetylacetonates", Catalysis Communications, 2011, pp. 1295-1297, vol. 12.

Chai et al., "Study of Preparation of 1,1,1,3-tetrachloropropane", Zhejiang Huagong Industry, 2010, pp. 1-3, 41(5).

Cristiano et al., Tetraalkylphosphonium Trihalides. Room Temperature Ionic Liquids as Halogenation Reagents, J. Org. Chem., 2009, pp. 9027-9033, vol. 74.

Evstigneev et al., "Initiated Chlorination of Tetrachloropropane", Khim. Prom., 1984, pp. 393-394, 16(7).

Fields et al., "Thermal Isomerization of 1,1-dichlorocyclopropanes", Chemical Communications, Jan. 1, 1967, 1081, No. 21.

Galitzenstein et al., "The Dehydrochlorination of Propylene Dichloride", Journal of the Society of Chemical Industry, 1950, pp. 298-304, vol. 69.

Gault et al., "Chlorination of Chloroform" Comptes Rendus Des Seances De L'Academie des Sciences, 1924, pp. 467-469, vol. 179.

Gerding et al, "Raman Spectra of aliphatic chlorine compounds: chloroethenes an chloropropenes", Recueil Jan. 1, 1955, pp. 957-975, vol. 74.

Hatch et al., "Allylic Chlorides. XV. Preparation and Properties of the 1,2,3Trichloropropenes". JACS, Jan. 5, 1952, pp. 123-126, vol. 74.

Hatch et al., "Allylic Chlorides. XVIII. Preparation and Properties of 1,1,3-tricholoro-2-fluoro-1-propene and 1,1,2,3-tetrachloro-1-propene". JACS, Jul. 5, 1952, pp. 3328-3330, 74(13).

Herzfelder, "Substitution in the Aliphatic Series", Berichte Der Deutschen Chemischen Gesellschaft, 26 (II), May-Aug. 1893, pp. 1257-1261, 26(2).

Ivanov et al., "Metal phthalocyanine-Catalyzed Addition of polychlorine-Containing Organic Compounds to C=C Bonds," Russian Chemical Bulletin, International Edition, Nov. 2009, pp. 2393-2396, 58(11).

Kang et al., Kinetics of Synthesis of 1,1,1,3,3-pentachlorobutane Catalyzed by Fe—FeCl3, Chemical Research and Application, Jun. 2011, pp. 657-660, 23(6).

Kharasch et al.,, "Chlorinations with Sulfuryl Chloride.I. The Peroxide-Catalyzed Chlorination of Hydrocarbons", JACS, 1939, pp. 2142-2150, vol. 61.

Khusnutdinov et al., CCl4 Attachment to Olefins Catalyzed by Chromium and Ruthenium Complexes. Impact of Water as a Nucleophilic Admixture, Oil Chemistry, 2009, pp. 349-356, vol. 4.

Kruper et al., "Synthesis of alpha-Halocinnamate Esters via Solvolytic Rearrangement of Trichloroallyl Alcohols", J Org Chem, 1991, pp. 3323-3329, vol. 56.

Leitch, "Organic Deuterium Compounds: V. The chlorination of propyne and propyne D-4", Canadian Journal of Chemistry, Apr. 1, 1953, pp. 385-386, 30(4).

Levanova et al.. "Thermocatalytic Reactions of Bromochloropropanes", Russian Journal of Physical Chemistry, Jan. 1, 1983, pp. 1142-1146, vol. 57.

Liu et al., "Progress in Synthesis of 1,1,1,3-tetrachloropropane", Guangzhou Chemicals, 2011, , pp. 41-42, 39(5).

McBee et al., , Utilization of Polychloropropanes and Hexachloroethane, Industrial and Engineering Chemistry, Feb. 1, 1941, pp. 176-181, 33(2).

Mouneyrat, "Effect of Chlorine on Propyl Chloride in the Presence of Anhydrous Aluminum Chloride" Bulletin de la Societe chimique de france, Societe francaise de chimie, vol. 3, No. 21, Jan. 1, 1899.

Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair et al., "Atom transfer radical addition (ATRA) of carbon tetrachloride and chlorinated esters to various olefins catalyzed by CP/Ru(PPh3)(PR3)Cl complexes", Inorganica Chimica Acta, 380 2012, 96-103.

Nguyen et al., "Condensation de chloroforme avec des olefins fluorees en milieu basique," Journal of Fluorine Chemistry, vol. 55, No. 3, Dec. 1, 1991, pp. 241-248.

Nikishin et al, "Reactions of Methanol and Ethanol with Tetrachloroethylene," N.D. Zelinskii Institute of Organic Chemistry, Academy of Sciences of the USSR, 2115-2119. Translated from Izvestiya Akademii Nauk SSSR, Seriya Khimicheskaya 1966, 12, 2188-2192.

Pozdnev et al., "Chlorination of chloroform and the conversion of methylene chloride manufacture still residues", Khim., Khim. Tekhnol. (1970) 70-4.

Rotshtein et al., "Isomer Distribution on Chlorination of Chloropropanes", Z. Organicheskoi Khimii, 2(9), pp. 1539-1542 (1966).

Semenov, "Selectivity of Photochemical Chlorination of Chloromethane in the Liquid Phase", Prikladnei Khimii, vol. 58, No. 4, pp. 840-845 (1985).

Shelton et al., "Addition of Halogens and Halogen Compounds to Allylic Chlorides. I. Addition of Hydrogen Halides," Journal of Organic Chemistry, 23, pp. 1876-1880 (1958).

Skell, et al., "Reactions of BrCl with alkyl radicals", Tetrahedron letters, vol. 27, No. 43, pp. 5181-5184, 1986.

Skell et al., "Selectivities of pi and sigma succinimidyl radicals in substitution and addition reactions, Response to Walling, WI-Taliawi and Zhao", JACS, vol. 105, No. 15, Jul. 1, 1983, p. 5125-5131.

Tanuma et al., "Partially Fluorinated Metal Oxide Catalysts for a Friedel-Crafts-type Reaction of Dichlorofluoromethane with Tetrafluoroethylene", Catal. Lett. (2010) 136:77-82.

(56) References Cited

OTHER PUBLICATIONS

Tobey et al., "Pentachlorocyclopropane 1" Journal of the American Chemical Society, vol. 88, No. 11, Jun. 1, 1996 pp. 2478-2481.

Urry et al., "Free Radical Reactions of Diazomethane with Reactive Bromopolychloroalkane", JACS, vol. 86, No. 9, May 5, 1964, p. 1815-1819.

Wang Chin-Hsien, Elimination Reactions of polyhaloprppanes under emulsion catalytic conditions to give Halopropenes, Synthesis, Teorg Thieme Verlag, Stuttgart, De, vol. 1982, No. 6, Jan. 1, 1982, pp. 494-496.

Zhao et al., "Research Progress on Preparation Technology of 1, 1, 2, 3-Tetrachloropropene," Zhejiang Chemical Industry, vol. 41, No. 6, p. 8-10 (2010).

Zheng et al., "Review of the Preparation of the low GWP alternative 1,3,3,3-tetrafluoropropene", Zhejiang Huagong (2010) 41(3), 5-7.

Levanova, et al., "Cholorination of Chloroolefins C3—C4", Doklady Chemistry, vol. 386, No. 4, 2002, 496-498.

Stevens, "Some New Cyclopropanes with a Note on the Exterior Valence Angles of Cyclopropane", JACS, Vo. 68, No. 4, 1945, 620-622.

Michigan Technological Univ., "Free-Radical Chlorination with Sulfuryl Chloride", Nov. 15, 2001, 1-7.

PROCESS FOR THE PRODUCTION OF CHLORINATED ALKANES

FIELD

The present invention relates to processes for the production of chlorinated alkanes. The processes are capable of adding multiple chlorine atoms in a one reactor system, and so, are particularly suitable for use in the production of, e.g., tetra- and pentachlorinated alkanes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, highly chlorinated alkanes, e.g., tetra- and pentachloroalkanes.

Unfortunately, these higher chlorides have proven difficult to manufacture using acceptable process conditions and in commercially acceptable regioselectivities and yields. For example, conventional processes for the production of pentachloropropanes provide unacceptable selectivity to the desired pentachloropropane isomer(s), i.e., 1,1,2,2,3-pentachloropropane, make use of suboptimal chlorinating agents, require the use of high intensity process conditions and/or catalyst systems that are difficult to utilize in large scale production processes and/or are limited to the addition of a single chlorine atom per reaction pass, and so must be repeated until the desired number of chlorine atoms has been added, with each additional step requiring additional capital, energy, and other cost investment.

It would thus be desirable to provide improved processes for the production of chlorocarbon precursors useful as feedstocks in the synthesis of refrigerants and other commercial products. More particularly, such processes would provide an improvement over the current state of the art if they provided a higher regioselectivity relative to conventional methods, made use of optimal chlorinating agents, required low intensity process conditions, made use of catalyst systems and/or initiators more amenable to use in large-scale processes, or were capable of the addition of multiple chlorine atoms per reaction pass as compared to conventional processes.

BRIEF DESCRIPTION

The present invention provides efficient processes for the production of highly chlorinated alkanes. More particularly, the processes make use of one or more nonmetallic iodides, or other nonmetallic precursors to at least one hypervalent iodine species, and/or low levels of elemental iodine as a catalyst for the addition of multiple chlorine atoms to alkanes, desirably as part of a mixed catalyst system further comprising at least one Lewis acid. The use of nonmetallic iodides are advantageous as compared to conventional processes, in that nonmetallic iodides are not as corrosive or volatile as elemental iodine when employed at conventional levels, and so, are more readily and conveniently incorporated into large scale manufacturing process. Further cost savings are provided in that low intensity process conditions, e.g., low temperatures, ambient pressure and minimal reactor residence time, are utilized.

In one aspect, the present invention provides a process for the production of chlorinated alkanes. The process comprises catalyzing the addition of at least two chlorine atoms to an alkane and/or alkene with a mixed catalyst system comprising one or more nonmetallic iodides, and/or less than 10,000 ppm elemental iodine and at least one Lewis acid. Although a nonmetallic iodide is used as part of the catalyst system, and in some advantageous embodiments, no iodine is added to the starting chlorinated alkane and/or alkene. In some embodiments, the one or more nonmetallic iodide may comprise aryl iodides, iodoso compounds, iodohalogens, or combinations of these. In some embodiments, the concentration of elemental iodine used, if any, may be from 1 ppm to 5000 ppm, or from 5 ppm to 1000 ppm, or from 10 ppm to 100 ppm. The source of chlorine atoms may comprise chlorine gas, sulfuryl chloride or a combination of these, and in some embodiments comprises sulfuryl chloride, which may also act as a diluent or solvent as well as a chlorine source. The alkane and/or alkene may initially be unchlorinated, or, may already comprise chlorine atoms, and may comprise any number of carbon atoms.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

As used herein, the term "nonmetallic iodide" is meant to include incorporate any nonmetallic compound, incorporating, or otherwise capable of providing or forming in a reaction mixture, at least one hypervalent iodine species. Typically, such compounds may further be characterized in that they comprise only nonmetal and iodine elements. The term "hypervalent", in turn, and as is understood by those of ordinary skill in the chemical arts, means a compound that has one or more elements bearing more than eight electrons in their valence shells.

The present invention provides efficient processes for the production of chlorinated alkanes. The present processes catalyzing the addition of at least two chlorine atoms to an alkane or an alkene with a mixed catalyst system comprising one or more nonmetallic iodides and at least one Lewis acid. The use of a nonmetallic iodide is advantageous, especially as compared to the use of elemental iodine (as is conventional in many process for the production of highly chlorinated propanes and propenes), as nonmetallic iodide does not present the volatility and corrosion issues that can be presented by elemental iodine when used at conventional levels.

Further, while conventional processes that employ nonmetallic iodides are taught to be limited to the addition of single chlorine atoms, it has now been discovered that, when utilized in combination with at least one Lewis acid, nonmetallic iodides not only can add multiple chlorine atoms, but further, are capable of adding multiple chlorine atoms in a highly regioselective manner.

Any nonmetallic iodide can be used in the mixed catalyst system, and those of ordinary skill in the art are expected to be familiar with many. Suitable examples include, but are not limited to, iodobenzene, halogenated iodobenzenes, phenylchloroiodonium chloride, diaryliodonium salts, iodinated polymers, iodoxy compounds, iodoso compounds, iodine mono- and trihalides, iodine oxides, and derivatives or combinations of any number of these.

In other embodiments, elemental iodine may be used, but at levels much lower than previously thought to be effective. That is, it has now been discovered that amounts of iodine much lower than conventionally utilized, i.e., 0.01 wt. %, provide improvements in yield and selectivity while yet not presenting the corrosion and volatility issues that may arise when these conventional levels are utilized. More specifically, amounts of elemental iodine of from 1 ppm to 5000 ppm, or from 5 ppm to 1000 ppm, or from 10 ppm to 100 ppm, have now surprisingly been discovered to provide selectivities to the desired chloropropanes of greater than 60%, in some cases greater than 70%, and in some cases greater than 80%. This is a significant improvement over processes wherein no iodine is used at all, wherein conversions of e.g., less than 60% can be seen. Since elemental iodine can be costly, significant cost savings are also provided by using the smaller amounts described herein. Combinations of one or more nonmetallic iodides and elemental iodine may also be used.

The mixed catalyst system used in the process also desirably comprises at least one Lewis acids. Any Lewis acid that at least marginally enhances the process can be utilized, and examples of these include, but are not limited to ferric chloride, antimony pentafluoride, boron trichloride, aluminum trichloride, and stannic chloride. Combinations of two or more of these may also be used, if desired. In some embodiments, anhydrous aluminum chloride may desirably be utilized as the at least one Lewis acid.

Generally speaking, enough of the mixed catalyst system should be utilized to provide some improvement to reaction process conditions (e.g., a reduction in required temperature) and desirably, reaction selectivity, but yet not be more than will provide any additional benefit, if only for reasons of economic practicality. For purposes of illustration only, then, it is expected that useful concentrations of the nonmetallic iodide, in a batch process, will range from 0.01% to 30% by weight with respect to the alkane and/or alkene, or from 0.1% to 20%, or from 1% to 10 wt. %, inclusive of all subranges therebetween. Surprisingly low levels of elemental iodine are effective, e.g., from 1 ppm to 5000 ppm, or from 5 ppm to 1000 ppm, or from 10 ppm to 100 ppm. Suitable amounts of the Lewis acid will range from 0.01% to 20% by weight each with respect to the dichlorinated alkane, or from 0.1% to 10%, or from 1% to 5 wt. %, inclusive of all subranges therebetween. For continuous processes, it is possible that much lower concentrations, e.g., as much as 5, or 10, or 15 or even 20 times lower will not only be effective, but be effective over the entire course of plant operability.

The at least two chlorine atoms are desirably supplied by chlorine gas, sulfuryl chloride, or both. Sulfuryl chloride ($SO_2Cl_2$), can also act as a solvent for the mixed catalyst systems and/or reactions, thereby assisting in the provision of an acceptable reaction rate and/or yield. And so, in some embodiments, sulfuryl chloride may desirably be used as the chlorinating agent.

In some embodiments, including those wherein chlorine is used as a chlorinating agent rather than sulfuryl chloride, a solvent may be used in the present processes. Desirably, any solvent will be inert to the desired chemistry, allow for adequate mass transfer during the chemical reaction, and create a homogenous phase to insure uniform reactivity throughout the reactor. Chlorocarbon solvents are especially well suited for the present processes due to their ease in handling and relative resistance to the desired chemistry, and many of these are known to those of ordinary skill in the art. For example, suitable chlorocarbon solvents include, but are not limited to carbon tetrachloride, methylene chloride, chloroform, 1,2,3-trichloropropane, 1,1,2,3-tetrachloropropane, and 1,1,2,2,3,3-hexachloropropane. In some embodiments, the chlorocarbon solvent may comprise methylene chloride or 1,2,3-trichloropropane.

The reaction conditions under which the process is carried out are advantageously low intensity. That is, low temperatures, e.g., of less than 100° C., or less than 90° C., or less than 80° C. or less than 70° C., or less than 60° C., may be utilized and the desired selectivities to the desired chlorinated alkanes yet be realized. In some embodiments, temperatures of from 40° C. to 90° C., or from 50° C. to 80° C., or from 55° C. to 75° C. may be utilized. Similarly, ambient pressure is suitable for carrying out the process, or pressures within 250, or 200, or 150, or 100, or 50, or 40, or 30, or 20, or even 10 psi, of ambient are suitable. Reactor occupancy may also be minimized with the desired selectivities yet seen—for example, reactor occupancy times of less than 20 hours, or less than 15 hours, or less than 10 hours, or less than 9, 8, 7, 6, or even 5 hours, are possible. The reactor may be any suitable liquid phase reactor, such as a batch or continuous stirred tank autoclave reactor with an internal cooling coil. A shell and multitube exchanger followed by vapor liquid disengagement tank or vessel can also be used.

The present process can make use of one or more alkanes or alkenes to produce the desired chlorinated alkanes. Alkanes or alkenes having any number of carbon atoms and that are desirably chlorinated with at least two chlorine atoms may benefit from application of the present process. Generally speaking, alkanes or alkenes comprising from 2-10 carbon atoms, or from 2-8 carbon atoms, or from 2-6 carbon atoms, or from 2-5 carbon atoms, or from 2-4 carbon atoms, are particularly suitable. In some embodiments, the alkane or alkene may comprise a propane or propene.

Similarly, the alkane and or alkene may be unchlorinated, or may comprise chlorine atoms prior to application of the process. That is, the alkane and/or alkene may comprise any number of chlorine atoms, including zero. To some degree, the number of chlorine atoms in the alkane or alkene will be limited by the number of carbon atoms, as well as the chlorinated alkane and/or alkene desirably produced. In some embodiments, the alkane and/or alkene may comprise from 0-4 chlorine atoms, or may comprise 1-3 chlorine atoms. In some embodiments, the alkane and/or alkene may be a mono-, di-, or trichlorinated propane, such as 1- or 2-chloropropane, 1,2-dichlorinated propane, and/or 1,1,2-trichlorinated propane.

The chlorinated alkane produced by the process will depend upon the alkane and/or alkene used as a starting material, and so, in some embodiments, and due to the commercial significance of trichlorinated alkanes having three to six carbon atoms, the use of one or more propanes, propenes, butanes, butenes, pentanes, pentenes, hexanes and hexanes as starting materials may be preferred. In one exemplary embodiment, a trichloropropane, e.g., 1,1,2-trichloropropane, is utilized as a starting material to produce a pentachloropropane, e.g., 1,1,2,2,3-pentachloropropane at regioselectivities of greater than 10:1, or greater than 20:1 or greater than 30:1, or even greater than 40:1, over other pentachloropropane products.

In one exemplary process, 1,1,2-trichloropropane is converted to 1,1,2,2,3-pentachloropropane at selectivities of, e.g., 30:1, or 40:1, or 50:1, or 60:1, or 70:1, or 80:1, or 90:1, or even 100:1 or greater, over other pentachloropropane products, by reacting 1,1,2-trichloropropane with sulfuryl chloride in the presence of iodobenzene at a temperature of from 55° C. to 75° C., ambient pressure and a reactor occupancy of less than five hours.

Some embodiments of the invention will now be described in detail in the following examples.

EXAMPLE 1

Chlorination of 1,1,2-trichloropropane to 1,1,2,2,3-pentachloropropane using iodobenzene as nonmetallic iodide, aluminum chloride as Lewis acid and sulfuryl chloride as chlorinating agent.

A product stream containing 26 wt % 1,1,2-trichloropropane, 61 wt % sulfuryl chloride, and 12 wt % based upon the total weight of the initial reaction mixture aluminum chloride is charged with 10 mol % aluminum chloride dissolved in 310 mol % sulfuryl chloride followed by 10 mol % iodobenzene. The resulting mixture is allowed to stir for 4 hours at a temperature of 70° C. and then cooled to ambient temperature prior to pouring the mixture into an ice bath. The resulting solution is filtered to remove the quenched catalyst byproduct and the resulting product mixture is analyzed by gas chromatography. The final organic phase is found to consist of >91% 1,1,2,2,3-pentachloropropane, with the remaining 9% comprising a mixture of tri-,tetra-, and hexachloropropane isomers.

EXAMPLE 2

Chlorination of 1,1,2-trichloropropane to 1,1,2,2,3-pentachloropropane using iododurene (2,3,5,6-tetramethyl-1-iodobenzene) as nonmetallic iodide, aluminum chloride as Lewis acid and sulfuryl chloride as chlorinating agent.

A product stream containing 26 wt % 1,1,2-trichloropropane, 61 wt % sulfuryl chloride, and 12 wt % based upon the total weight of the initial reaction mixture aluminum chloride is charged with 10 mol % aluminum chloride dissolved in 200 mol % sulfuryl chloride followed by 10 mol % iododurene. The resulting mixture is allowed to stir for 3 hours at a temperature of 70° C. and then cooled to ambient temperature prior to pouring the mixture into an ice bath. The resulting solution is filtered to remove the quenched catalyst byproduct and the resulting product mixture is analyzed by gas chromatography. The final organic phase is found to consist of >84% 1,1,2,2,3-pentachloropropane, with the remaining 16% comprising a mixture of tri-,tetra-, and hexachloropropane isomers.

EXAMPLE 3

Chlorination of 1,1,2-trichloropropane to 1,1,2,2,3-pentachloropropane using low levels of elemental iodine, aluminum chloride as Lewis acid, chlorine as chlorinating agent, and methylene chloride as chlorocarbon solvent.

A product stream is prepared by feeding chlorine gas at 30 sccm through a starting mixture of 22.6 wt % 1,2-dichloropropane, 1.3 wt % aluminum chloride, and 76.1 wt % methylene chloride at 130 psig and 70° C. until GC analysis indicates that the starting dichloropropane has undergone 68% conversion to give 1,1,2-trichloropropane as the major intermediate species. This stream is charged with 35 ppm elemental iodine dissolved in 15 mL of methylene chloride based on initial dichloropropane within the reaction mixture. The resulting mixture is allowed to stir until 36.1% conversion of the 1,1,2-trichloropropane intermediate is observed to give the desired pentachloropropane and its precursor 1,2,2,3-tetrachloropropane in 82.3% selectivity over the undesired byproducts of 1,1,2,2,3,3-hexachloropropane and 1,1,2,3-tetrachloropropane. When viewed in light of Example 4, this example shows that virtually the same conversion of 1,1,2-trichloropropane with virtually the same selectivity to the desired pentachloropropane when a significantly lower amount of elemental iodine is used than is conventional. When viewed in combination with Example 5, this example shows that even these low levels of iodine result in significantly greater selectivities to the desired pentachloropropanes than no elemental iodine at all.

EXAMPLE 4

Chlorination of 1,1,2-trichloropropane to 1,1,2,2,3-pentachloropropane using conventional levels of iodine, aluminum chloride as Lewis acid, chlorine as chlorinating agent, and methylene chloride as inert chlorocarbon solvent.

A product stream is prepared by feeding chlorine gas at 30 sccm through a starting mixture of 22.6 wt % 1,2-dichloropropane, 1.3 wt % aluminum chloride, and 76.1 wt % methylene chloride at 130 psig and 70° C. until GC analysis indicates that the starting dichloropropane has undergone 69.7 wt % conversion to give 1,1,2-trichloropropane as the major intermediate species. This stream is charged with 0.57 wt % elemental iodine dissolved in 15 mL of methylene chloride based on initial dichloropropane within the reaction mixture. The resulting mixture is allowed to stir until 33.0% conversion of the 1,1,2-trichloropropane intermediate is observed to give the desired pentachloropropane and its precursors in 85.4% selectivity over the undesired byproducts of 1,1,2,2,3,3-hexachloropropane and 1,1,2,3-tetrachloropropane.

EXAMPLE 5

Chlorination of 1,1,2-trichloropropane to 1,1,2,2,3-pentachloropropane in the absence of elemental iodine using aluminum chloride as Lewis acid, chlorine as chlorinating agent, and methylene chloride as inert chlorocarbon solvent.

A product stream is prepared by feeding chlorine gas at 30 sccm through a starting mixture of 22.6 wt % 1,2-dichloropropane, 1.3 wt % aluminum chloride, and 76.1 wt % methylene chloride at 130 psig and 70° C. until GC analysis indicates that the starting dichloropropane has undergone 71.5 wt % conversion to give 1,1,2-trichloropropane as the major intermediate species. This stream is charged with 15 mL of methylene chloride. The resulting mixture is allowed to stir until 28.3% conversion of the 1,1,2-trichloropropane intermediate is observed to give the desired pentachloropropane and its precursors in 53.9% selectivity over the undesired byproducts of 1,1,2,2,3,3-hexachloropropane and 1,1,2,3-tetrachloropropane.

EXAMPLE 6

Chlorination of 1,1,2-trichloropropane to 1,1,2,2,3-pentachloropropane using low levels of iodobenzene, aluminum chloride as Lewis acid, chlorine as chlorinating agent, and methylene chloride as inert chlorocarbon solvent.

A product stream is prepared by feeding chlorine gas at 30 sccm through a starting mixture of 22.6 wt % 1,2-dichloropropane, 0.65 wt % aluminum chloride, and 76.6 wt % methylene chloride at 130psig and 70° C. until GC analysis indicated that the starting dichloropropane has undergone 76% conversion to give 1,1,2-trichloropropane as the major intermediate species. This stream is charged with 210 ppm of iodobenzene that was dissolved in 10 mL of methylene chloride. The resulting mixture is allowed to stir until 40.1% conversion of the 1,1,2-trichloropropane intermediate is observed to give the desired pentachloropropane and its precursors in 75.6% selectivity over the undesired byproducts of 1,1,2,2,3,3 -hexachloropropane and 1,1,2,3 -tetrachloropropane.

When viewed in combination with Example 4, this example shows that extremely low levels of iodobenzene are as effective as conventional levels of elemental iodine, i.e., low levels of iodobenzene can provide conversions of 1,1,2-trichloropropane within 10% of those provided by conventional amounts of elemental iodine and selectivities to the desired pentachloropropanes within 10% of those provided by conventional amounts of elemental iodine.

The invention claimed is:

1. A process for the production of chlorinated propanes comprising catalyzing the addition of at least two chlorine atoms to a propane with a catalyst system comprising at least one Lewis acid and one or more nonmetallic iodides and/or from 1 ppm to 5000 ppm elemental iodine.

2. The process of claim 1, wherein the source of chlorine atoms comprises chlorine gas, sulfuryl chloride or a combination of these.

3. The process of claim 1, wherein the Lewis acid comprises aluminum chloride.

4. The process of claim 1, wherein the process is conducted in the presence of a chlorocarbon solvent.

5. The process of claim 4, wherein the chlorocarbon solvent comprises methylene chloride or 1,2,3-trichloropropane.

6. The process of claim 1, wherein the propane comprises from 0-4 chlorine atoms.

7. The process of claim 6, wherein the propane is a trichloropropane.

8. The process of claim 1, wherein the chlorinated propane comprises a pentachloropropane.

9. The process of claim 8, wherein the chlorinated alkane comprises 1,1,2,2,3-pentachloropropane.

10. The process of claim 1, wherein the nonmetallic iodide comprises iodobenzene, chlorinated iodobenzene, and derivatives thereof, phenylchloroiodonium chloride and derivatives thereof, iodinated polymers, iodine trihalides, or combinations of any number of these.

11. The process of claim 10, wherein the nonmetallic iodide comprises iodobenzene.

12. The process of claim 10, wherein the nonmetallic iodide comprises pentachloroiodobenzene.

13. The process of claim 1, wherein the process is a liquid phase process.

14. The process of claim 1, wherein the process provides a selectivity to a desired chlorinated propane of at least 75%.

* * * * *